Dec. 17, 1963 J. C. MIKKELSEN Plant Pat. 2,328
POINSETTIA PLANT
Filed Jan. 7, 1963
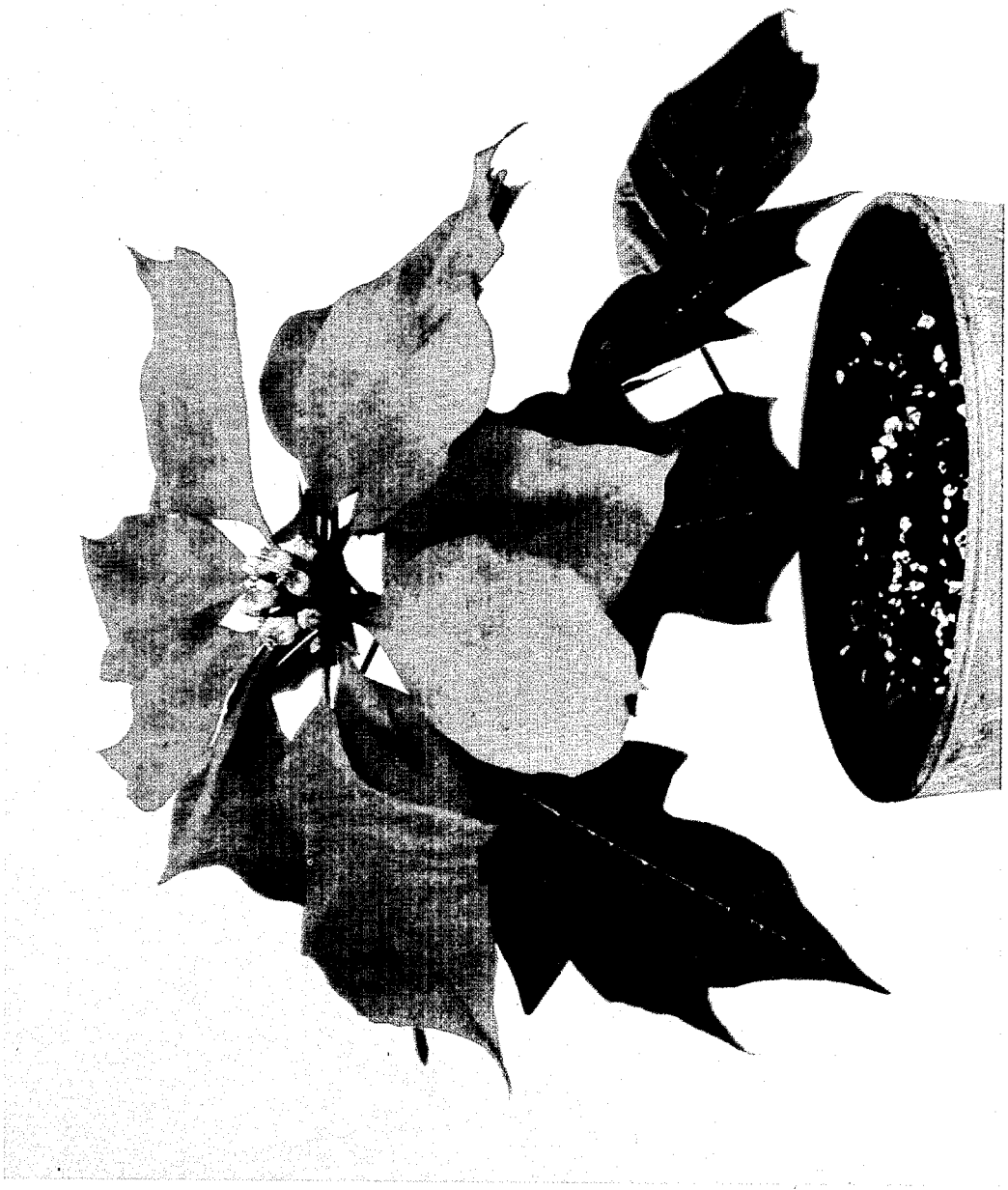
Inventor.
J. C. Mikkelsen
By: Robb & Robb
Attorneys.

United States Patent Office

Plant Pat. 2,328

Patented Dec. 17, 1963

2,328

POINSETTIA PLANT

James C. Mikkelsen, 1803 W. 13th St., Ashtabula, Ohio

Filed Jan. 7, 1963, Ser. No. 249,964

1 Claim. (Cl. Plt.—86)

The present invention relates to a new and distinct variety of poinsettia plant (botanically known as *Euphorbia pulcherrima*), which was originated by me by crossing an unnamed and unpatented seedling of the variety "Barbara Ecke Supreme" (Plant Patent No. 1,055) and the variety "Ecke's White" (Plant Patent No. 1,802).

As the result of this breeding, I have produced a new variety of poinsettia plant which is a definite improvement over most other poinsettia varieties, particularly from a commercial standpoint, and which is distinctly different from the parent varieties, as well as from all other varieties of which I am aware, as evidenced by the following unique combination of characteristics which are outstanding therein:

(1) A semi-dwarf plant habit;

(2) Rigid stems which do not require staking;

(3) Relatively short leaves and bracts which facilitate shipping with far less likelihood of injury than present commercial varieties;

(4) Distinctive and attractive red colored bracts which do not droop with old age;

(5) Relatively small flowers which do not drop excessive pollen or nectar;

(6) Ease of culture without requiring exacting growing techniques to prevent early flowering such as is usually required with most previously known varieties; and (7) Excellent keeping qualities which assure long lasting and relatively low plants that are especially useful for home decorations.

Asexual reproduction of my new variety by vegetative cuttings propagated under mist at Ashtabula, Ohio, shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Ashtabula, Ohio, under regular commercial practices:

Parentage: Seedling.

*Seed parent.*—An unnamed seedling of "Barbara Ecke Supreme."

*Pollen parent.*—"Ecke's White."

Form: Semi-dwarf; compact; upright; no branching.

Habit of growth: Slower growing than present commercial varieties; no self-branching; semi-dwarf; compact; upright.

Rooting habit: Roots more quickly than either parent variety; roots are quite fibrous and appear to be less susceptible to root rot organisms than present commercial varieties.

Blooming habit: Normal.

Blooming season: Late November and December; very suitable for forcing.

Foliage: Alternate; borne on stems at a slight upward angle ranging from about 15° to 20°; does not tend to fall off as the plant matures; above normal quantity.

*Size.*—Medium (about 4 inches to 6 inches long).

*Shape.*—Short and stubby in contrast to longer and narrower leaves of present commercial varieties; oval-pointed.

*Texture.*—Upper side—becomes semi-glossy at maturity; veins have a definite recessed and dendritic pattern. Under side—dull; veins have definite protrusion.

*Margin.*—Clean-cut and distinct.

*Color.*—New foliage—upper side: Pod Green, Plate 061; lower side: Pod Green, Plate 061/1. Old foliage—upper side: Spinach Green, Plate 0960; lower side: Spinach Green, Plate 0960/2.

Disease resistance: Resistant to botrytis and mildew, as determined by comparison with other plants grown under the same cultural conditions at Ashtabula, Ohio, and which were infected with these diseases.

Bracts: Become more long-pointed as flowers develop; development continues over a much longer period of time than other red poinsettias and bracts retain a horizontal position for many months; color holds well for several months; bracts have slight twisting formation at the very tip end.

*Color.*—Upper side—Currant Red, Plate 821/2. Under side—Rhodonite Red, Plate 0022.

Flowers:

*Borne.*—Continuously for several months, with many flowers per stem in regular clusters in varying stages of development; borne on short and strong stems.

*Quantity of bloom.*—Relatively abundant; continuous during one season of 3 to 4 months; flowers gradually drop off after maturity, but new ones continue to develop as the flower stems continue to grow.

*Buds.*—Small; borne on light green stems corresponding to color of buds. Color—Scheeles Green, Plate 860/1.

Reproductive organs:

*Stamens.*—Quite numerous; from about ⅛ inch to ¼ inch long. Color—Currant Red, Plate 821/2.

*Pollen.*—Color—Canary Yellow, Plate 2.

*Styles.*—Color—Blood Red, Plate 820.

*Ovaries.*—Color—Scheeles Green, Plate 860/1.

*Nectar cups.*—Color—Lemon Yellow, Plate 4/1.

General observations: In comparison with the pollen parent, "Ecke's White," which is characterized by white colored bracts, my new variety has red colored bracts which are distinctly different; as compared with "Barbara Ecke Supreme," the new variety is more rigid and upright and therefore not as "wild" or limp, has shorter and broader leaves, has bracts that are not quite as bright red in color and are somewhat shorter than those of this variety, but more numerous and more rigid and permanent, while there is less nectar and pollen on the flowers, cuttings propagate much easier, the foliage and bracts are maintained on the plant longer even when subjected to more severe conditions, and the new variety ships and handles better than "Barbara Ecke Supreme."

I claim:

A new and distinct variety of poinsettia plant, substantially as herein shown and described, characterized particularly as to novelty by a semi-dwarf plant habit, rigid stems which do not require staking, short leaves and bracts which facilitate shipping and are substantially less subject to injury, distinctive and attractive bracts of currant red general color tonality and which do not droop with age, small flowers which are free of excessive pollen or nectar, ease of propagation without requiring exacting growing techniques to prevent early flowering, and excellent keeping qualities, with consequent long-lasting plants useful for home decorations.

No references cited.